United States Patent [19]

Gartside et al.

[11] Patent Number: 5,510,557
[45] Date of Patent: Apr. 23, 1996

[54] ENDOTHERMIC CATALYTIC DEHYDROGENATION PROCESS

[75] Inventors: Robert J. Gartside, Summit; Cemal Ercan, Bloomfield; Kandasamy M. Sundaram, Old Bridge, all of N.J.

[73] Assignee: ABB Lummus Crest Inc., Bloomfield, N.J.

[21] Appl. No.: 202,835

[22] Filed: Feb. 28, 1994

[51] Int. Cl.$^6$ .................................................. C07C 5/333
[52] U.S. Cl. ............................. 585/654; 502/38; 208/134
[58] Field of Search ................................. 585/500, 654; 208/134; 502/38

[56] References Cited

U.S. PATENT DOCUMENTS

| | | | |
|---|---|---|---|
| 2,328,234 | 8/1943 | Seguy | 502/38 |
| 2,485,906 | 10/1949 | Mills, Jr. | 502/38 |
| 3,904,703 | 9/1975 | Lo et al. | 585/441 |
| 4,041,099 | 8/1977 | Hutson, Jr. | 585/444 |
| 4,581,339 | 4/1986 | Bhatt et al. | 585/654 |
| 4,704,497 | 11/1987 | Gottlieb et al. | 585/654 |
| 5,235,071 | 8/1993 | Ueda et al. | 502/113 |
| 5,258,349 | 11/1993 | Dalla Betta et al. | 502/330 |

OTHER PUBLICATIONS

Haynes, et al., *Chemical Engineering Science*, vol. 47, No. 9–11, pp. 2927–2934 (1992).

*Primary Examiner*—Asok Pal
*Assistant Examiner*—Patrick J. Neill
*Attorney, Agent, or Firm*—Elliot M. Olstein; Raymond J. Lillie

[57] ABSTRACT

Catalytic dehydrogenation wherein feed is passed in one direction through the bed in a first cycle and heating gas is passed in an opposite direction in a second cycle to provide the endothermic heat of reaction and regenerate catalyst. The operation is controlled to balance properly heat absorbed during dehydrogenation and heat input during regeneration; e.g., by having catalyst of different activities over the length of the bed.

11 Claims, 8 Drawing Sheets

ENDOTHERMIC CATALYTIC DEHYDROGENATION PROCESS

This invention relates to dehydrogenation and more particularly to an endothermic dehydrogenation process. Still more particularly, this invention relates to an endothermic dehydrogenation process wherein the dehydrogenation catalyst is taken off-stream to both effect regeneration thereof and heating thereof to provide the endothermic heat of reaction for dehydrogenation.

Dehydrogenation is an endothermic, equilibrium-limited reaction. The extent of conversion attainable by reaction is limited by thermodynamics with higher temperatures favoring higher conversion.

In some processes for endothermic catalytic dehydrogenation of a feed, the feed is passed over a fixed be of catalyst. In order for the reaction to occur, heat must be supplied. In one process, the catalyst is placed in tubes and the heat for the reaction is supplied by transfer through the walls of the tubes. In a second, the heat is supplied by diluting the feedstock with a gas that acts as a heat carrier. Both feed and diluent are heated to a temperature above that required for reaction and then passed over the catalyst. The endothermic reaction absorbs heat from the gases themselves and the heat content of the diluent plus feedstock allows the reaction to absorb heat and thus reach a high conversion without reducing the temperature of the mixture to a point where the reaction would stop.

In a third process, the heat required for reaction is absorbed from the bed of solids (catalyst or catalyst plus inert material). Hydrocarbon feed is passed over a hot bed of catalyst without dilution. The reaction absorbs heat from the solids and lowers the temperature of the catalyst bed. At some point in time, the bed is too cool to sustain reaction. The reactor is periodically taken off-stream where the bed materials are reheated by contact with a heated gas. That gas could be steam, air, nitrogen, helium, etc. the only requirement being that the gas or gas mixture not be detrimental to the catalyst. Specifically however, the gas mixture contains oxygen and thus serves the dual purpose of regenerating the catalyst by removal of carbonaceous material by combustion and imparting heat from that combustion to the catalyst for use in the endothermic on-stream dehydrogenation process.

As is known in the art, the dehydrogenation reactor is taken off-stream and directly contacted with a heated oxygen containing stream for a period of time, and thereafter placed back on-stream. Thus, the dehydrogenation and catalyst reheat/regeneration procedure involves an on-stream dehydrogenation cycle for a period of time, followed by an off-stream regeneration/reheat cycle for a period of time, followed by an on-stream operation, etc. In this process, the hydrocarbon feed and the regeneration gas pass through a common inlet during the alternate cycles and flow in a similar or co-current direction over the catalyst bed.

All of the above-mentioned processes have identified different solutions to adding heat to a fixed bed of catalyst. Heat addition and/or heat removal from a fixed bed of catalyst is difficult and places certain restrictions on the optimal designs for a reaction that occurs in such a bed.

It is also known in the art that changing the flow direction of the feedstock to a fixed bed reactor on a periodic basis can alter the temperature profile over the bed for that reaction. This has been applied for catalytic exothermic reactions in order to allow for process heat recovery by having cooler feed gas be preheated by the residual hotter portion of the bed of catalyst following a change or reversal of flow direction.

The concept has been examined for endothermic catalytic dehydrogenation of ethyl benzene to styrene. In the current steady state process for the production of styrene, ethylbenzene and steam are passed over a bed of catalyst continuously. The ethylbenzene reacts endothermically to form styrene absorbing heat and lowering the temperature of the gas. The steam acts as a heat carrier providing sensible heat for the reaction and thus allowing it to proceed to higher conversions. It is similar to the second process mentioned above. There is no cyclic operation.

Certain studies, The Application of Reverse Flow Reactors to Endothermic Reactions, Haynes, Thomas N., et at, Chem Engr Science, vol 47, No. 9–11, pp 2927–2932, 1992, have shown that the current steady state continuous process for the endothermic dehydrogenation of ethylbenzene to styrene may be improved by a combination of operating the reactor in a periodic fashion with on-stream and off-stream cycles and using a hot inert gas, such as steam, during the off-stream reheat cycle. The steam is introduced at the opposite end of the reactor from the feed and thus flows in the "reverse" direction. This creates a temperature profile where the highest temperature is at the end of the reactor (in terms of feed flow direction) as opposed to at the beginning of the reactor.

Their analysis for the ethylbenzene to styrene reaction shows that the optimum reaction conditions are represented by a very high ratio of regeneration steam flow to feed hydrocarbon flow and a maximum temperature difference between the hydrocarbon feed and the regeneration steam. The improved performance of the reaction system is described as being the result of a) reducing the dilution of the feed to allow for a faster reaction and b) a more favorable temperature profile. All of the reaction heat is supplied by the sensible heat of the regeneration gas and there is no interaction between the cycles except for the fact that sensible heat is transferred to the reaction from the solids during the on-stream cycle and from the regeneration gas to the solids during the off-stream cycle.

A portion of the advantages attributed to the "reverse flow" process are actually due to operation in a transient cyclic manner.

The present invention is directed to improving the operation of a catalytic endothermic dehydrogenation process which involves an on-stream dehydrogenation cycle, and an off-stream regeneration cycle to provide heat for the endothermic dehydrogenation and to also regenerate the catalyst.

BRIEF DESCRIPTION OF DRAWINGS

The invention will be further described with reference to the following drawings; however, the scope of the invention is not limited thereby.

Specifically, the invention is directed to improving the operation of processes for the dehydrogenation of lower paraffins or olefins or mixtures thereof. Lower paraffins are defined as those with carbon numbers less than 6, for example propane to propylene, butane to butadiene, and isobutane to isobutylene. Further, the invention is directed at processes where the regeneration gas contains oxygen for removal of the carbonaceous deposits from the reaction cycle. It is to be understood, however, that the invention is not limited to such feeds.

In accordance with an aspect of the present invention, there is provided a catalytic endothermic dehydrogenation process wherein in the dehydrogenation or first cycle, a dehydrogenation feed is passed through a catalyst bed to effect the endothermic dehydrogenation of the feed, and wherein in a heating or second cycle, a heating gas is passed through the catalyst bed in a direction opposite or counter-current to the dehydrogenation feed to provide heat for the catalyst bed for the endothermic dehydrogenation reaction.

Applicant has found that by changing from co-current to counter-current flow through the bed with respect to the dehydrogenation cycle and heating cycles, and by balancing the location of heat absorbed during the dehydrogenation cycle and location of the heat input during the regeneration cycle, the overall performance of the dehydrogenation reaction with respect to conversion and/or selectivity can be improved.

The location of the heat absorbed and heat input during the dehydrogenation and heating cycles can be balanced by controlling the operating conditions in the respective cycles and/or by adjusting overall catalyst activity and/or by using different catalyst activities within the bed, as hereinafter described in further detail.

Applicant has found that during the dehydrogenation or reaction cycle, the amount of heat that is removed from the bed differs dependent upon the location along the axial length of the bed. Specifically, the amount of heat removed during the reaction cycle at a particular point in the bed is a function of the amount of reaction that occurred at that particular point. The extent of reaction is dependent upon the temperature of the bed at that location during the cycle, the catalyst activity at that point, and the extent of reaction that has occurred within the bed up to that point. Since catalytic dehydrogenation reactions are equilibrium limited, if extensive reaction has occurred prior to reaching a particular point in the bed, the reaction may be close to equilibrium and further dehydrogenation may not occur in spite of favorable catalyst activity and temperature.

Under the conditions of the prior art co-current flow and of the counter-current flow of this invention, several non-selective degradation reactions also occur in addition to the dehydrogenation reaction. These reactions include the reaction of either the feed or product to lighter gaseous fuel materials such as methane and the degradation reaction of products to carbonaceous materials that impact catalytic activity. These reactions are not equilibrium limited and continue even when the main dehydrogenation reaction has reached equilibrium limits. The reaction to gaseous fuel products represents a loss in reaction selectivity but does not impact the subsequent regeneration cycle. The reaction to coke materials however provide heat input to the subsequent regeneration cycle. Further, the location where the cooling reaction occurs defines specifically at what location along the axial length of the bed the heat is subsequently released during the regeneration cycle.

Heat for the endothermic reaction is provided by a combination of sensible heat transfer from the gas to the cooler solids, by the combustion of coke deposited during the reaction cycle and by the reaction of oxygen absorbed by the catalyst during regeneration with the feed (or a reduction gas if used). Typically, about 50% of the heat is provided locally by coke combustion and feed oxidation and 50% by sensible heat transfer from the regeneration gas. As discussed above, the location of the heat provided by the coke is determined by the extent of product degradation at that point in the bed and is a function of product concentration, temperature, and catalyst activity. The catalyst will absorb oxygen uniformly and thus will oxidize feed or reduction gas and release that heat uniformly over the bed length. Sensible heat transfer will occur until the temperature of the gas and solids are equal. For both the co-current system of the prior art and the counter-current flow of the present invention, there is considerably greater solids area per unit gas feed such that the heat from the gas is quickly released. The bed is reheated in a manner such that a temperature front moves down the bed slowly in the direction of flow. Where heat transfer has occurred, the bed is at the regeneration gas temperature. The temperature front does not however pass through the bed since the regeneration cycle is terminated prior to this point being reached. In those locations where the temperature front has not reached, the local temperature cycles around a value determined by a balance of heat provided by the coke combustion and that removed by reaction.

Figure 1:
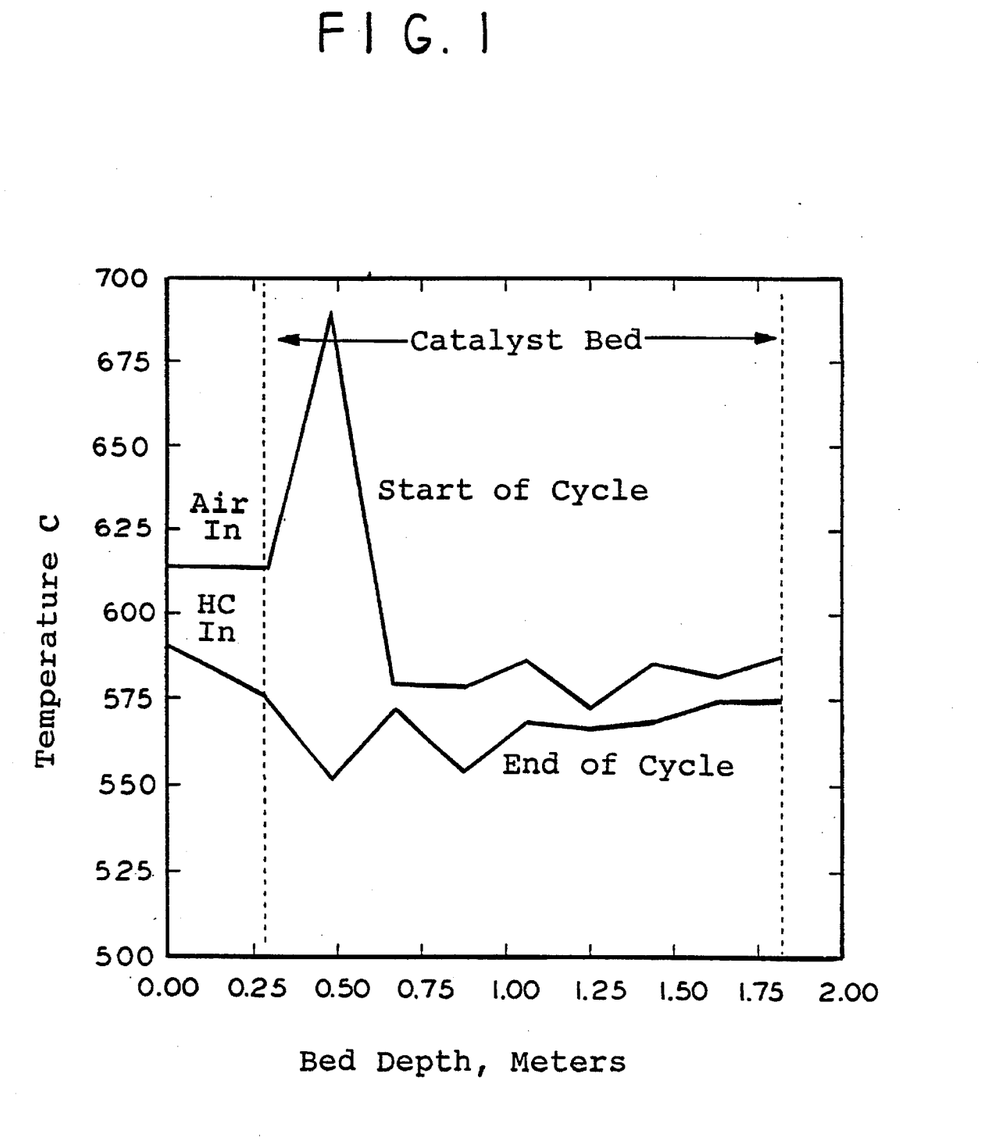
FIG. 1 is a temperature profile for a co-current dehydrogenation and regeneration cycles in accordance with the prior art.
Figure 2:
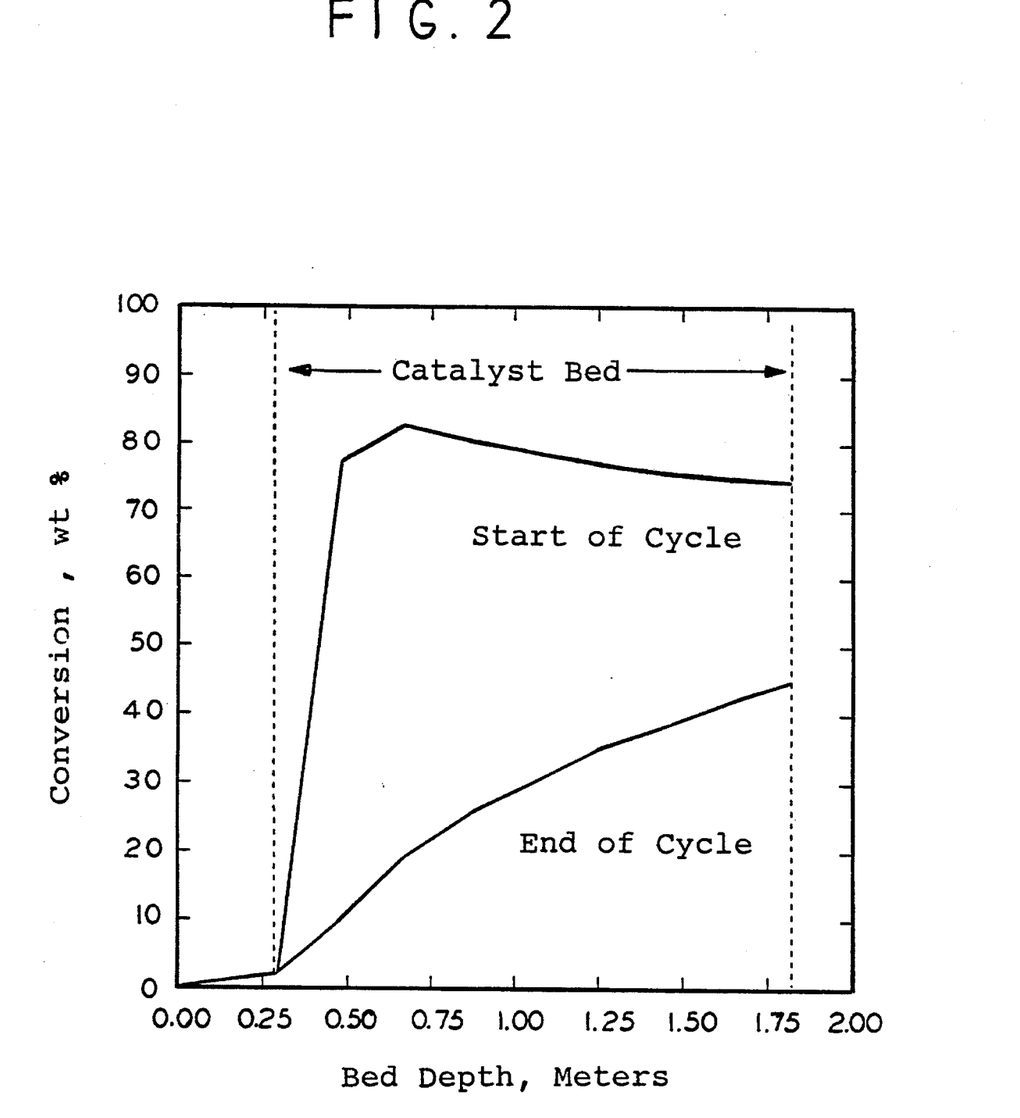
FIG. 2 is a temperature profile for counter-current flow dehydrogenation and regeneration cycles in accordance with the invention.
Figure 3:
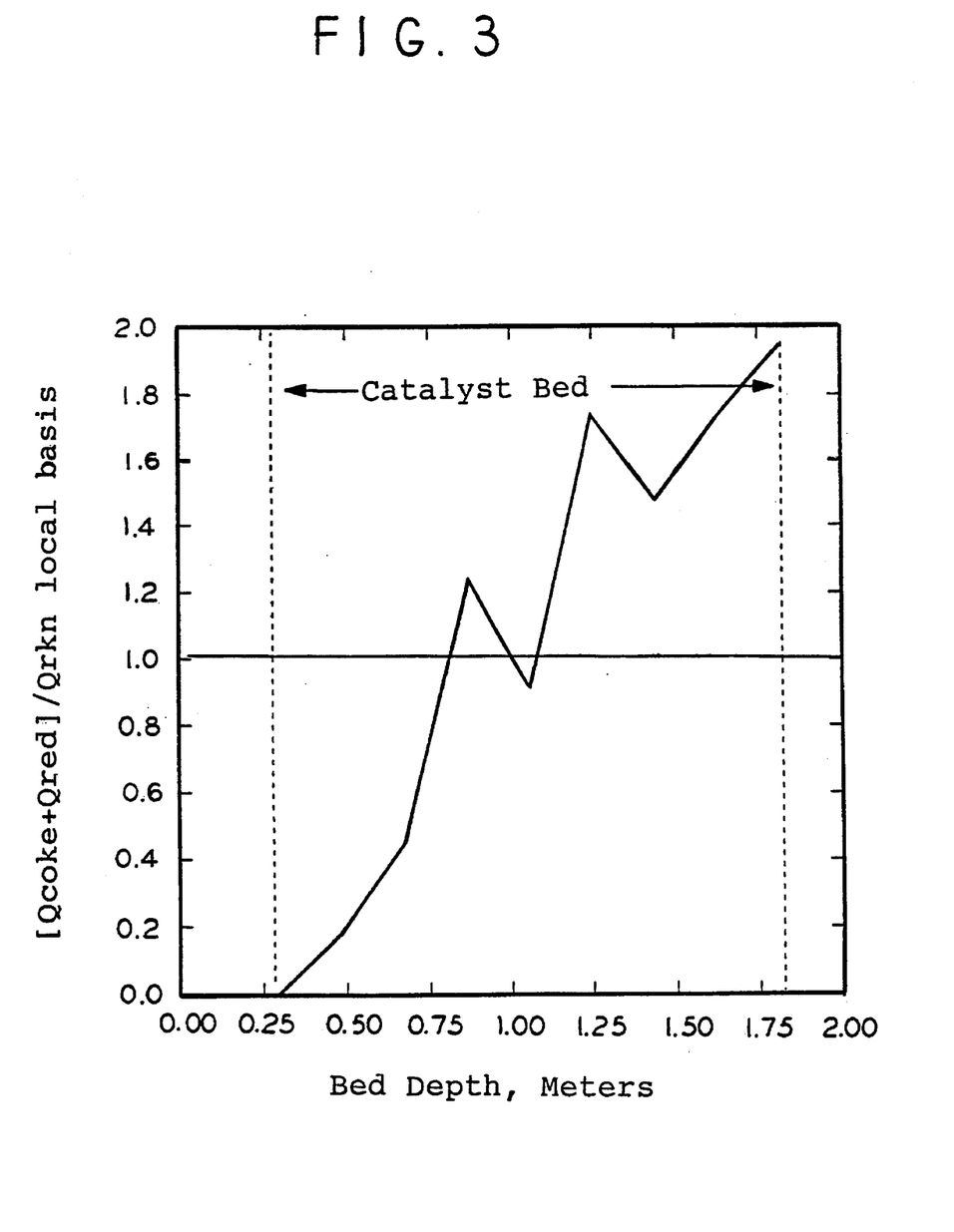
FIG. 3 is a plot of the ratio of heat generated locally by coke combustion and feed or reduction gas oxidation to heat absorbed during dehydrogenation integrated over the entire cycle time for co-current flow dehydrogenation.

In the co-current system of the prior art, the regeneration gas is introduced at the same end of the catalyst bed as the hydrocarbon feed. This creates the maximum temperature point at the beginning of the bed in terms of the reaction cycle. Further, the catalyst is loaded at uniform concentration and activity throughout the bed. When the feed is introduced during the dehydrogenation cycle, the point of maximum reaction hence heat removal is at that point. Not only is the temperature the highest resulting in the highest reaction velocity coefficient, but the reaction is also farthest from equilibrium resulting in maximum driving forces for reaction. The reaction rapidly reaches equilibrium and high product concentrations are achieved at relatively short axial distance into the bed. The high product concentration leads to degradation reactions to fuel components and coke and these reactions occur toward the end of the bed. Importantly, the coke is deposited at the opposite end of the reactor from where the heat released would be most beneficial. Thus the majority of the heat released from the coke cannot be used for reaction resulting in an inefficient use of the catalyst bed. This heat must however be removed to avoid an excessive buildup of temperature at the end of the bed which could deactivate the catalyst. FIG. 1 presents a temperature profile of the prior art as generated from the cyclic operation of hydrocarbon and air. Shown are the temperature profiles at the start of hydrocarbon and the end of the hydrocarbon cycle. The reheat or regeneration cycle restores the temperature of the solids to the curve indicated by start of hydrocarbon cycle. FIG. 2 presents a plot of the conversion profile over the bed as a function of time on stream. It can be seen that the majority of the conversion takes place initially upon contacting the bed up to the point where sufficient heat has been removed from the top of the bed by the endothermic reaction to push the conversion deeper into the bed. FIG. 3 presents a plot relating the ratio of heat generated locally via coke combustion and feed or reduction gas oxidation to heat absorbed in the dehydrogenation reaction integrated over the entire cycle time. It can be seen for the entire lower portion of the bed, more heat is generated than consumed. In order for a stable reactor to exist without excessive temperatures in the bottom, this heat must be removed by heat transfer from the catalyst bed to the regeneration gas. This is subsequently recovered in downstream equipment. Removal of this heat represents an inefficiency in terms of the reactor.

In the co-current system of the prior art, if higher conversions are desired, more heat must be supplied to the reactor. This is accomplished by adding more sensible heat via regeneration gas flow which raises the temperature and increases reaction. The total increase in conversion is defined by the increase in sensible heat input plus the increase in coke combustion due to a higher coke yield at higher conversion. Alternately, the flow of feedstock could be reduced thus increasing both the time for reaction and the heat per unit feed. Practically, however, the latter decreases reactor system performance by reducing overall production and is less preferred. However, the increase in temperature and reaction is principally at the top of the bed resulting increased degradation to fuel components and coke and an even greater inefficiency in terms of using the heat produced by combustion of that coke. This places limits on the performance of that system. In practice, conversions in excess of 60% are not practical due to extensive loss of reaction selectivity and potential for high temperatures in the bed.

Applicants have found that by changing the flow direction of the regeneration gas, and by adjusting the overall catalytic activity of the bed, and/or by creating catalyst activity profiles over the bed, these limitations can be removed and conversions significantly greater than 60% can be achieved.

Figure 4:
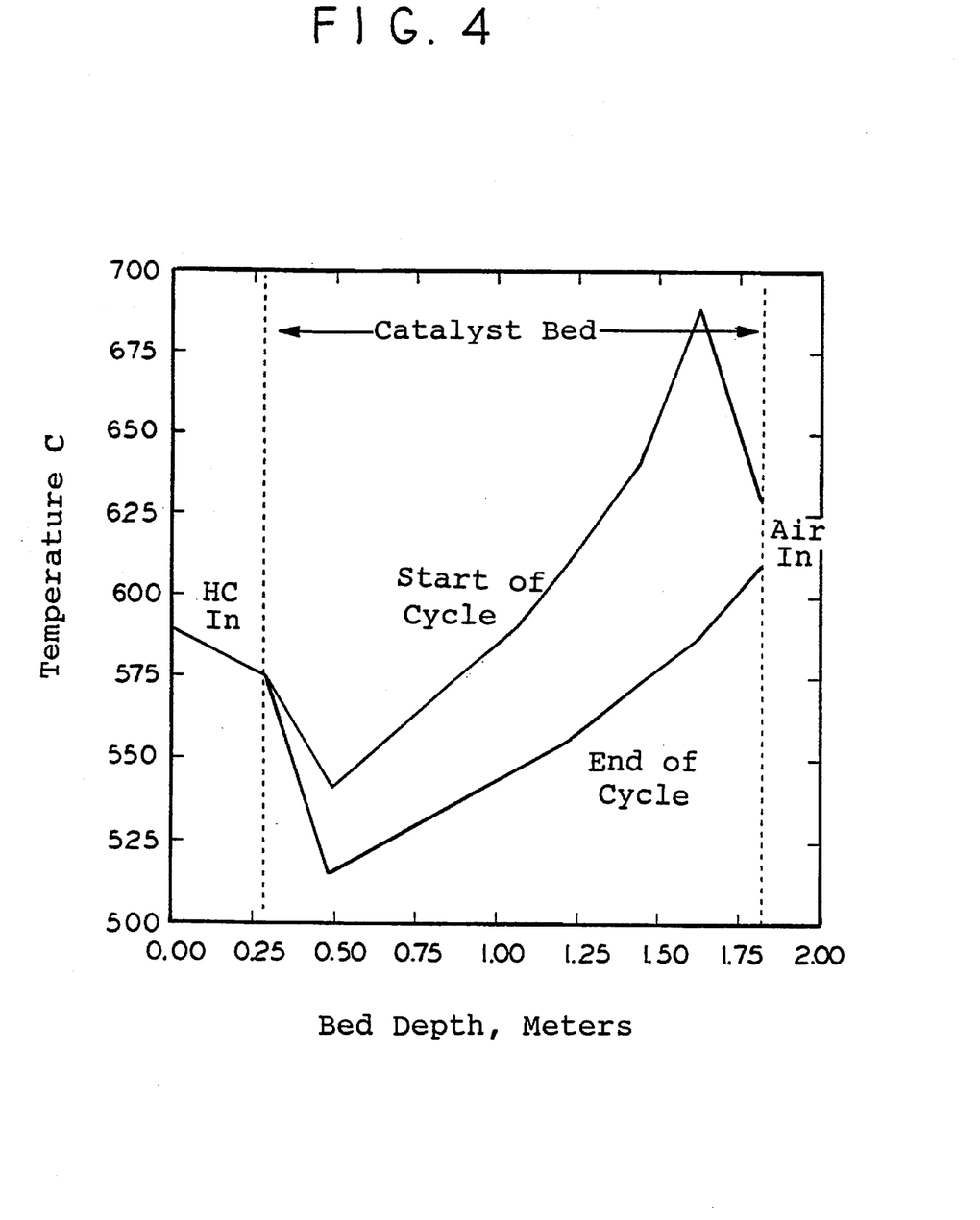
FIG. 4 is a plot of temperature profile for a counter-current flow operation at the conditions of FIG. 1 at both the start and end of the reaction cycle.
Figure 5:
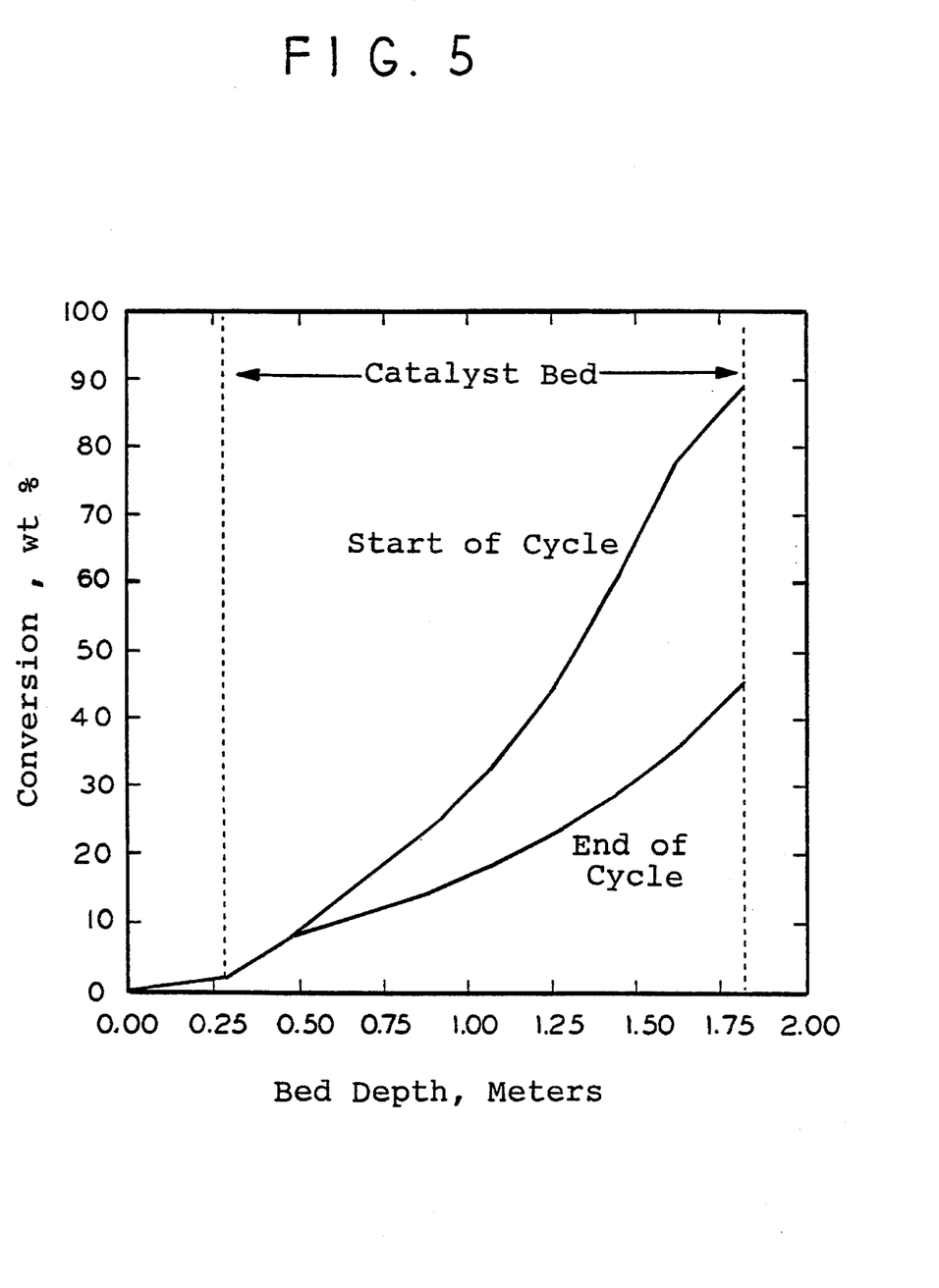
FIG. 5 is a plot of the conversion profile for counter-current flow in accordance with the invention.

In the system of the present invention, the regeneration gas is introduced at the opposite end of the reactor from the feed hydrocarbon. This places the highest temperature at the end of the reactor and thus provides the most favorable conditions for continued reaction with respect to equilibrium. Further, the heat generated by the coke within the system occurs at the end of the reactor and is pushed back into the bed for use as reaction heat by the flow of regeneration gas instead of being pushed out of the bed for downstream heat recovery. This increases the performance of the reaction system. FIG. 4 is a plot of the temperature profile created under similar operating conditions to the prior art of FIG. 1 at both the start and end of the reaction cycle. As can be seen, the temperatures rise uniformly over the bed length. At the beginning of the bed, the temperatures are low but the reaction is far from equilibrium. Significant reaction occurs in spite of the lower temperatures. As the hydrocarbon proceeds down the bed, the temperatures increase and the equilibrium limits continually move away presenting always more favorable reaction conditions. The regeneration gas enters at the higher temperature end and leaves the bed at a low temperature since the sensible heat has been expended moving through the bed. Compared to the prior art where both hydrocarbon and regeneration gas enters at the same end, more heat is removed from the regeneration gas in a given cycle thus increasing its performance. FIG. 5 is a plot of the conversion profile for the counter-current flow case showing how the conversion occurs much more uniformly over the bed length. This leads to better heat utilization and better reaction selectivity since the residence time of products subject to continued reaction and degradation is reduced.

Figure 6:
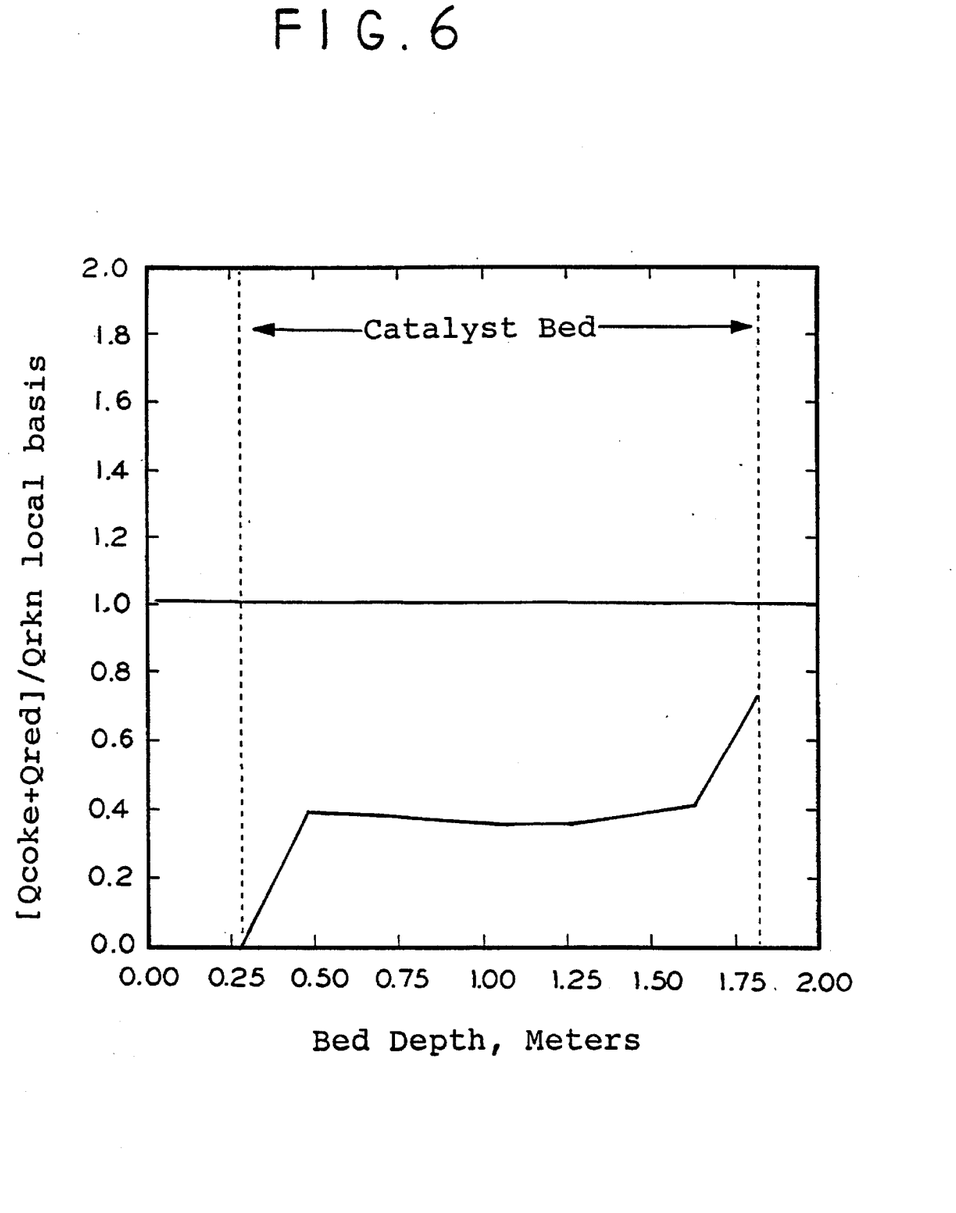
FIG. 6 is a plot of locally generated heat versus heat of reaction for counter-current flow as in FIG. 2.

The shift in temperature profile created in part by reversing the flow has also a beneficial effect on heat utilization within the bed. FIG. 6 is a plot of locally generated heat versus heat of reaction absorbed at that location (similar to FIG. 2) for the counter-current flow case. As can be seen, for essentially the entire length of the reactor, the local heat generated represents approximately 50% of the heat absorbed. This is in close approximation to the overall heat balance. This is a result of achieving a uniform conversion profile over the length of the reactor which thus defines a uniform heat absorption over the length of the reactor and allows for maximum efficiency in heat utilization.

Applicants have also found that certain operating conditions and certain bed catalyst activity levels and catalyst activity profiles with axial distance are important in achieving uniform conversion and hence optimum reactor performance in counter-current flow. These variables influence the temperature profiles created under counter-current flow conditions and hence the reaction performance. The advantages of counter-current flow for the endothermic catalytic dehydrogenation of lower paraffins and the importance of the operational variables will be illustrated in the examples below.

EXAMPLE 1

Comparison of Base Prior Art and Counter-Current Flow at Identical Conditions [B7A vs REVB7A]

A catalyst bed is loaded with 67% vol chromium based dehydrogenation catalyst and 33% vol. inert alumina. These are mixed uniformly and loaded into the reactor vessel. The packed bed of catalyst is contacted with 30,000 Mt/hr of propane feed for a period of 9 minutes. The hydrocarbon had been preheated to a temperature of 590° C. and the reaction takes place at 0.5 atm absolute pressure. This cycle is followed by contact with a 210,000 Mt/hr of air for 9 minutes. The air stream has been preheated to 614° C. and 0.125 kg/sec of fuel is injected simultaneously with the air raising its temperature to 690° C. The air inlet is identical to the hydrocarbon inlet and both flows traverse the catalyst bed in the same direction. The average conversion achieved for the 9 minute cycle is 55.29 wt % and the propylene yield is 46.94 wt % for a reaction selectivity of 83.09 wt %. The yield of coke in this reaction is 1.43% wt. The conversion falls from 74.1% to 44.8% as heat is removed from the bed.

The identical Catalyst bed is contacted with the identical hydrocarbon flow and the identical air flow, the only difference being that the air is introduced at the point of hydrocarbon exit. The reactor thus operates in counter-current flow. The hydrocarbon conversion has increased by 11% to 66.25 wt %. The overall reaction selectivity has increased slightly from 83.09 to 83.18 wt %. The propylene yield is 55.26 and the coke yield is 1.47 wt %. The actual conversion for this case falls from 88.7 to 45.3% over the 9 minute cycle. As can be seen, changing the flow direction of one flow has resulted in a substantial increase in conversion at identical process conditions with no net increase in coke yield. This is a result of the more efficient utilization of the heat in the reactor.

Effect of catalyst layering

Higher catalyst concentration at top of the bed where the hydrocarbon first enters and less at the bottom at the point where the hydrocarbon leaves the bed leads to increased reaction at the top due to the higher catalyst concentration which compensates for the lower temperature at that point. Higher temperature at the bottom compensates for lower activity at the bottom to keep the reaction going without excessive degradation. This also leads to a smoother coke profile over the bed. This also leads to a reduction in variation in conversion with time. Advantages are improved stability, less cycle variation and improved selectivity.

EXAMPLE 2

Effect of Layering the Catalyst

The catalyst bed of Example 1 contained a total of 85 MT of catalyst. As can be seen from Example 1, changing the flow to counter-current has resulted in a substantial increase in conversion but at the expense of a wide variation in conversion over the cycle. While the prior art variation was 29.3 wt % (74.1 to 44.8), the variation over the cycle for counter-current flow was 43.3%. This increase could have negative impact on downstream separation equipment. A series of variations in catalyst loading was made and the results are presented as Table 1.

As can be seen, it is advantageous to place the catalyst in distinct layers within the bed. When more catalyst is loaded near the top of the bed (greater concentration as in Layer I and Layer 2), the overall variation in conversion over the cycle time is reduced substantially. One can also see by this example that is important to maintain sufficient catalyst at the bottom of the reactor near the hydrocarbon outlet. This allows the reaction to take advantage of the higher temperatures at this point without the limitation of catalyst concentration. Layer 3 uses the mirror image of the catalyst activity profile of layer 1. As can be seen, this is detrimental to reactor performance. The variation has increased substantially as has the coke. While the exact optimum profile for catalyst will be dependent upon the specifics of the catalyst activity and the process conditions employed, the catalyst should be loaded into layers where the top 50% of the bed contains catalyst at a higher concentration than the bed average and the bottom 50% contains catalyst at a lesser concentration than the bed average. Further, at no point should the catalyst concentration be lower than 20% by volume.

In this case, the identical catalyst is loaded in different concentrations admixed with inert. A similar effect can be achieved by loading catalyst of differing activity created by different composition in layers.

TABLE I

Effect of Catalyst Layering
Counter-Current Flow with Process Conditions of Example 1

| Case | Conversion wt % | Selectivity wt % | Conversion Variation wt % | Yield C3H6/Coke wt % |
|---|---|---|---|---|
| Base Case Uniform Catalyst (67 vol %) | 66.25 | 83.18 | 43.3 | 55.3/1.47 |
| Layer 1 Top(33%) 100% Mid(33%) 85% Btm(33%) 20% | 59.37 | 84.35 | 31.07 | 50.0/1.06 |
| Layer 2 Top(50%) 80% Btm(50%) 50% | 64.9 | 83.7 | 36.7 | 54.9/1.31 |

TABLE I-continued

Effect of Catalyst Layering
Counter-Current Flow with Process Conditions of Example 1

| Case | Conversion wt % | Selectivity wt % | Conversion Variation wt % | Yield C3H6/Coke wt % |
|---|---|---|---|---|
| Layer 3 Top(33%) 20% Mid(33%) 85% Btm(33%) 100% | 67.2 | 80.9 | 53.0 | 53.4/1.96 |

EXAMPLE 3

Effect of AIR/HC Ratio

As mentioned above, increasing the flow of regeneration gas compared to the flow of hydrocarbon will add more heat to the bed and increase conversion and temperature. However, for the counter-current flow reaction to occur in an optimal manner, the reaction should occur uniformly over the bed. If too little regeneration gas flow is used, there will be too little heat in the bed and low conversion will result. Unlike the ethylbezene-styrene system reported, there is a significant penalty if the regeneration gas flow is too high. By increasing the regeneration gas flow too high, the temperature at the bottom of the bed will become too high and excessive conversion and product degradation will occur.

The prior art as related to ethylbenzene to styrene technology as described in Haynes, et al supra shows that counter-current flow case has advantages over the continuous fixed bed technology at higher regeneration gas flow (steam). They state the benefits as resulting from a % combination of higher heat input and higher partial pressure of the feed via reduction of dilution. The greater the heat input for a given hydrocarbon feed flow, the higher the conversion that will be attained. Increased heat input to the reactor is most easily achieved by increasing the flow of regeneration gas which thus provides additional sensible heat.

Applicants have discovered however that there is an optimum for counter-current flow when dehydrogenating lower paraffins and using an oxygen containing regeneration gas. This optimum is created as a result of the increased degradation reactions at higher conversions for lower paraffins and the simultaneous production of coke during the reaction cycle which gives rise to high temperatures in the regeneration cycle when using air.

Figure 7A:
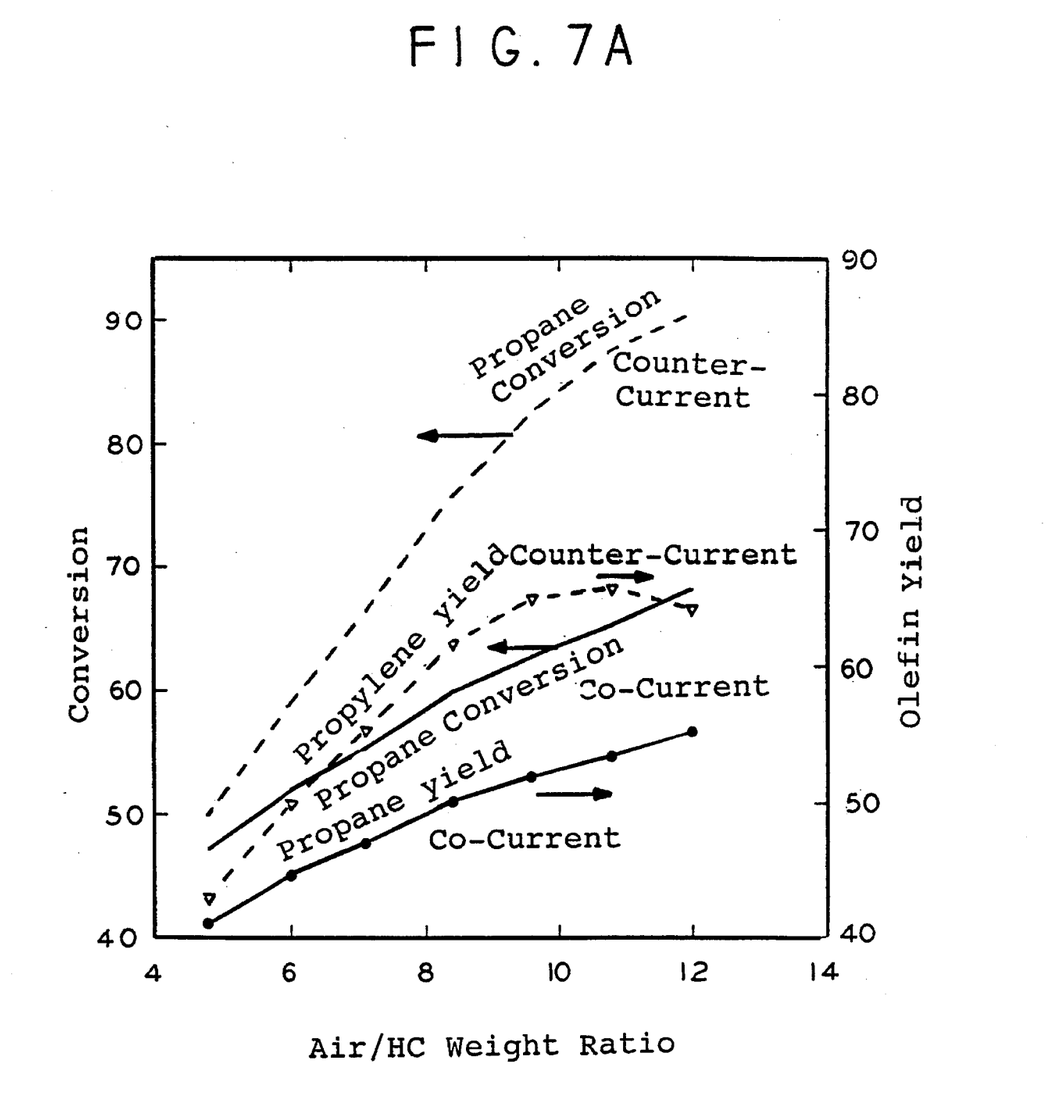
FIG. 7A is a plot of propane conversion and propylene yield for both co-current and counter-current flow operations at varying air to hydrocarbon ratios.

For the case of Example 1, all other conditions have been held constant and the flow of air during the fixed 9 minute regeneration cycle has been varied. The propane conversion and propylene yield are shown on FIG. 7A. As the air/HC weight ratio increased from 7.0 to 12.0, the cocurrent or prior art case showed a gradual increase in conversion from 55 to 68%. Selectivity to propylene decreased from 84.8 wt % to 79.2%. Note however that the net propylene yield still increased over the entire range. However for the counter-current flow case, while the conversion increased from 66.3 to 90.5% with the same increase in air/HC weight ratio, there is a peak in propylene yield defining an optimum ratio under this set of conditions.

Thus the preferred range for air/HC ratio for lower paraffin dehydrogenation is front 4.8 to 10.0. Below 4.8, the present invention will not show an advantage compared to the prior art. Above a ratio of 10, the loss in selectivity for counter-current flow will be such that the economic advantages of the higher conversion will be lost.

Figure 7B:
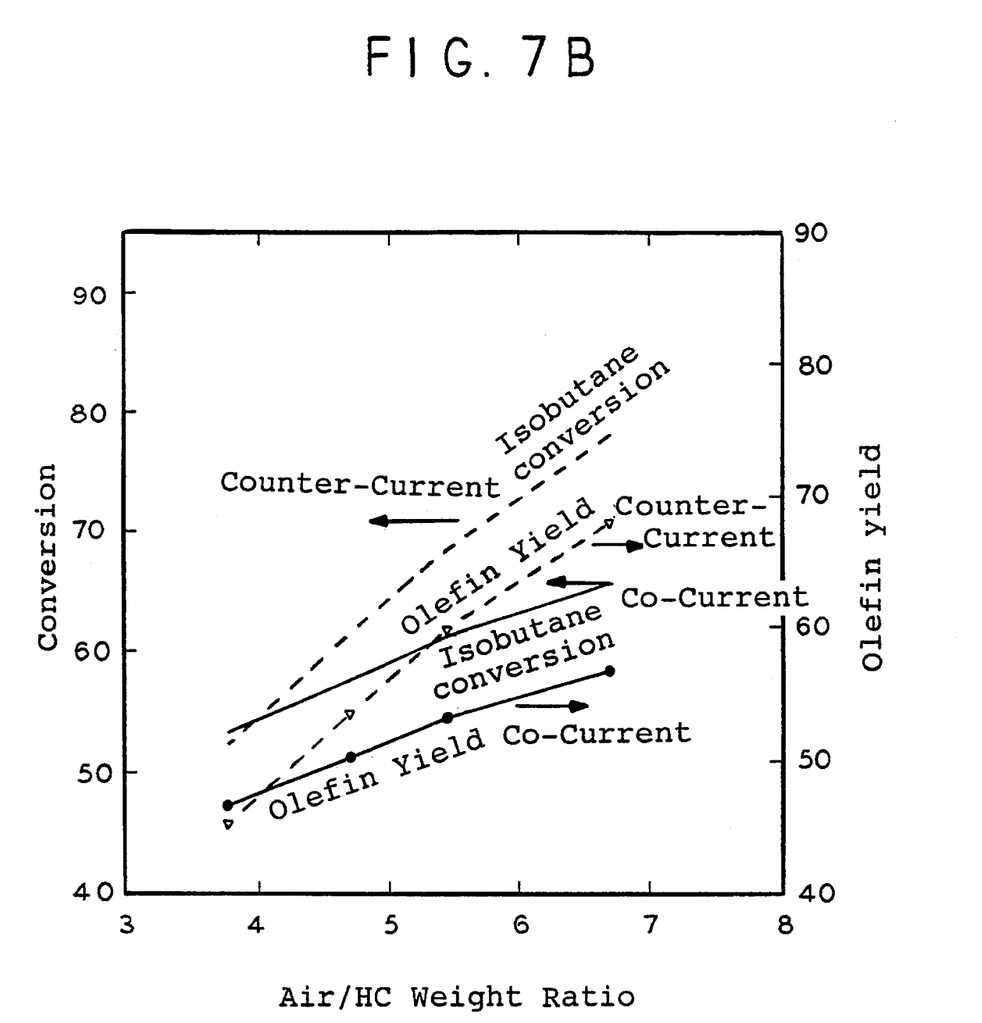
FIG. 7B is plot of isobutane conversion and isobutylene yield for both co-current and counter-current flow operations at varying air to hydrocarbon ratios.

This point is illustrated further by FIG. 7B. Using isobutane as a feed, the air/HC ratio was varied under otherwise identical conditions from 3.8 to 6.7. At low air/HC ratios, there is no incentive for reverse flow.

When the heat input to the reactor in the system of the prior art is low, the overall temperatures are low and the reaction is slowed to the point where it occurs in the center of the bed but at low conversions. At higher heat inputs, the reaction moves progressively closer to the top of the bed and the heat utilization performance deteriorates even though conversion is increased. In counter-current flow, at low heat input, most of the reaction occurs at the end of the bed and heat utilization is low, it increases with increasing heat input but reaches a maximum when the conversion profile becomes biased to the front of the reactor (similar to the cocurrent flow). This results in increased degradation.

EXAMPLE 4

Effect of Pressure

Hydrocarbon partial pressure provides the driving force for the reaction. Increasing pressure increases reaction rate and thus moves the reaction toward the top of the catalyst bed, Note that the rates of all reactions including degradation are increased. Increasing the pressure of operation has the positive effect of reducing subsequent product compression costs provided the degradation of product is not excessive. The extent of degradation that occurs depends upon the temperature/conversion profiles for the specific case. Increasing the pressure of operation has negative consequences for the prior art system but positive results for the counter-current flow system. This is shown in Table 2. For the case where all other process conditions are held constant, the pressure of reaction was increased from 0.5 atm absolute to 1.1 atm absolute for both the prior art and the present invention. There is a substantial loss in yield for the prior art system which is greater than the savings generated from reduced compression costs. This is not the case for the present invention. The yield of isobutylene is essentially the same and the compression savings result in an overall economic benefit.

TABLE 2

Effect of Pressure
Isobutane Dehydrogenation

| | Pressure atm | Conversion wt % | Selectivity wt % | IC4H8 yield wt % |
|---|---|---|---|---|
| Prior Art | 0.5 | 57.7 | 87.3 | 50.3 |
| Prior Art | 1.1 | 51.5 | 82.0 | 42.3 |
| Invention | 0.5 | 61.6 | 88.3 | 53.6 |
| invention | 1.1 | 63.5 | 85.3 | 53.0 |

Air/HC = 4.75

Description of Preferred Embodiment

As hereinabove indicated, in an embodiment of the present invention, the catalyst bed is layered in a manner such that there is a decrease in catalyst activity from the hydrocarbon feed inlet to the outlet, i.e, if hydrocarbon feed is introduced at the top of the reactor, the catalyst activity decreases from top to bottom. The change in catalyst activity may be achieved by decreasing the catalyst concentration from top to bottom, i.e., combining catalyst with inert, with the higher catalyst concentration being at the top of the bed. As an alternative, catalysts of different activity may be layered from top to bottom, with the higher activity catalyst being at the top of the bed.

Where catalyst layering is employed, over the length of the bed there may be two or more layers of catalyst. In one embodiment, the catalyst activity at the hydrocarbon feed inlet is greater than the average catalyst activity of the bed and at the product end of the bed, the catalyst activity is less than the average catalyst activity of the bed.

In employing counter-current flow in accordance with the present invention, in a preferred embodiment, the catalyst activity over the length of the bed (in some cases such activity may be essentially the same over the length of the bed and in other cases, as hereinabove described, the catalyst may be layered over the length of the bed to provide different catalyst activities) is coordinated with the other reaction conditions, in particular, hydrocarbon partial pressure and regenerating gas to hydrocarbon ratio to achieve desired conversion and selectivity and a proper heat balance between the reaction (endothermic) and regeneration (exothermic) portions of the cycle.

In a preferred embodiment of the present invention, when air is employed as the regenerating gas, the air to hydrocarbon ratio is from 4:1 to 10:1 and reaction pressure is from 0.3 to 2.0 atm. In most cases, the reaction temperature is from 450° C. to 700° C.

Thus, in an embodiment of the invention, at a desired level of conversion, the catalyst activity in the bed is coordinated with pressure and regenerating gas to hydrocarbon feed ratio taking into account the heat generated in regeneration of the catalyst to provide for a heat balance between the reaction and regeneration cycles whereby the heat input during regeneration does not exceed the heat withdrawn during reaction. A convenient manner of determining whether or not heat input during the heat cycle does not exceed the heat removed in the dehydrogenation reaction cycle is to determine the temperature of the bed at one or more fixed points at the beginning of successive reaction cycles. If without a change in operating parameters which effect bed temperature, the temperature at a fixed point or points does not essentially increase from the beginning of one dehydrogenation cycle to another dehydrogenation cycle, the heat input in the heating cycle does not exceed the heat removed in the dehydrogenation reaction cycle.

Numerous modifications and variations of the present invention are possible in light of the above teachings, and, therefore, within the scope of the appended claims, the invention may be practiced otherwise than as particularly described.

What is claimed is:

1. A catalytic endothermic dehydrogenation process, comprising:

in a first cycle passing a dehydrogenation feed through a dehydrogenation catalyst bed from an inlet end of the bed to an outlet end of the bed to effect dehydrogenation of the feed; and in a second cycle passing a heating gas through the dehydrogenation catalyst bed from the outlet end to the inlet end to provide heat to the catalyst bed for the endothermic dehydrogenation and to regenerate the catalyst by combusting carbonaceous deposits, wherein the catalyst bed is layered with the catalyst layer in the bed at the inlet end having an activity greater than the catalyst layer in the bed at the outlet end.

2. The process of claim 1 wherein the catalyst bed has a first catalyst at the inlet end and a second catalyst at the outlet end with the first catalyst being more active than the second catalyst.

3. The process of claim 1 wherein the catalyst bed has a higher concentration of catalyst at the inlet end than at the outlet end.

4. The process of claim 1 wherein there are more than two layers of catalyst in the bed, wherein catalyst activity decreases from layer to layer from the inlet end to the outlet end.

5. A catalytic endothermic dehydrogenation process, comprising:

in a first cycle passing a dehydrogenation feed of a lower hydrocarbon through a dehydrogenation catalyst bed from an inlet end of the bed to an outlet end of the bed to effect dehydrogenation of the feed; and in a second cycle passing a heating gas through the dehydrogenation catalyst bed from the outlet end to the inlet end to provide heat to the catalyst bed for the endothermic dehydrogenation and to regenerate the catalyst by combusting carbonaceous deposits, wherein the catalyst bed is layered with the catalyst layer in the bed at the inlet end having an activity greater than the catalyst layer in the bed at the outlet end.

6. The process of claim 5 wherein the heating gas contains oxygen.

7. The process of claim 6 wherein the heating gas is air.

8. The process of claim 7 wherein the air to hydrocarbon ratio based on the hydrocarbon used in the first cycle and air used in the second cycle is from 4:1 to 10:1.

9. The process of claim 7 wherein the pressure for the first and second cycle is from 0.3 to 2.0 atm.

10. A catalytic endothermic dehydrogenation process, comprising:

in a first cycle, passing a dehydrogenation feed of a lower hydrocarbon through a bed of dehydrogenation catalyst to dehydrogenate said feed endothermically; and in a second cycle, passing heated air through said catalyst bed in a direction opposite to that of the dehydrogenation feed to provide heat to said catalyst bed for the endothermic dehydrogenation reaction and to regenerate the catalyst, wherein the ratio of the heated air used in said second cycle to said dehydrogenation feed used in said first cycle is from 4:1 to 10:1.

11. The process of claim 10 wherein the pressure for each of the first and second cycles is from 0.3 atm to 2.0 atm.

* * * * *